US006518311B2

(12) United States Patent
Kozak et al.

(10) Patent No.: US 6,518,311 B2
(45) Date of Patent: Feb. 11, 2003

(54) USE OF BRANCHED-CHAIN FATTY ACIDS AND DERIVATIVES THEREOF FOR THE TREATMENT OF PAIN

(75) Inventors: Alexander Kozak, Rehovot (IL); Revital Duvdevani, Ramat Gan (IL); Firas M. Younis, Kfararara (IL)

(73) Assignee: D-Pharm Ltd., Rehovot (IL)

( * ) Notice: Subject to any disclaimer, the term of this patent is extended or adjusted under 35 U.S.C. 154(b) by 0 days.

(21) Appl. No.: 09/888,958

(22) Filed: Jun. 25, 2001

(65) Prior Publication Data

US 2002/0042445 A1 Apr. 11, 2002

Related U.S. Application Data

(63) Continuation-in-part of application No. 09/462,533, filed as application No. PCT/IL98/00316 on Jul. 7, 1998, now Pat. No. 6,251,946.

(30) Foreign Application Priority Data

Jul. 9, 1997 (IL) .................................................. 121268

(51) Int. Cl.$^7$ .............................................. A01N 32/18
(52) U.S. Cl. ........................... 514/613; 554/35; 554/79; 562/512; 564/192
(58) Field of Search ........................... 514/613; 554/35, 554/79; 562/512; 564/192

(56) References Cited

U.S. PATENT DOCUMENTS

| 4,846,991 A | 7/1989 | Suzue et al. ................ 252/89.1 |
| 5,278,300 A | 1/1994 | Hasegawa et al. ............ 536/53 |

FOREIGN PATENT DOCUMENTS

| EP | 0632008 A1 B1 | 1/1995 | ........... C07C/53/50 |

Primary Examiner—Deborah D. Carr
(74) Attorney, Agent, or Firm—Davidson, Davidson & Kappel, LLC

(57) ABSTRACT

The present invention relates to compounds and pharmaceutical compositions useful for treating pain. The invention also relates to methods of treating or alleviating pain in mammals, comprising administering to a mammal suffering from pain, a pain-alleviating amount of a compound of the general formula (I) or (II).

31 Claims, 1 Drawing Sheet

USE OF BRANCHED-CHAIN FATTY ACIDS AND DERIVATIVES THEREOF FOR THE TREATMENT OF PAIN

REFERENCES TO RELATED APPLICATIONS

This application is a continuation-in- part of U.S. Ser. No. 09/462,533, filed on Apr. 11, 2000, now U.S. Pat. No. 6,251,946 now allowed, which is a national phase entry of International application No. PCT/IL98/00316 filed on Jul. 7, 1998, the disclosures of which are hereby incorporated by reference.

FIELD OF THE INVENTION

The present invention relates to methods for the treatment of pain. More particularly, the invention relates to the use of certain branched-chain fatty acids (BFAs) and derivatives thereof in the treatment of pain in mammals and in particular in humans.

BACKGROUND OF THE INVENTION

Pain is a complex sensation and is the most common symptom of disease. Pain which is classified as somatogenic may be nociceptive pain which is due to a noxious stimulus (chemical, thermal, mechanical etc.) that activates pain receptors, or neuropathic pain which results from dysfunction of the central or peripheral nervous system and is often poorly localized.

Pain may also be classified as being acute or chronic in nature. Acute pain is usually a result of injury (e.g. trauma or disease), it lasts a short time and is typically resolves as the injured tissue heals or soon after. Chronic pain is usually defined broadly and arbitrarily as a pain persisting for over one month beyond the resolution of an acute tissue injury, pain persisting or recurring for more than 3 months, or pain associated with tissue injury that is continued or progressed [The Merck Manual, 1999].

Several pain syndromes are difficult to classify according to these criteria. These include, for example, chronic headache and continuous acute pain produced by the invasion of body tissues in malignant diseases.

Neuropathic pain is a common type of pain which can develop after injury to the nervous system and is usually a chronic pain. Neuropathic pain may result by trauma, central nervous system (CNS) pathology (e.g. stroke, spinal cord injury), by diseases such as diabetes, herpes zoster, or late stage of cancer, or by chemical injury. It may also develop after amputation.

The long-lasting neural mechanisms associated with chronic pain differ from those observed in acute pain [Loeser and Melzack (1999) Lancet 353: 1607–9]. Accordingly, also the pharmaceutical agents used to treat the various pain syndromes are different. It is well known that drugs that are useful against acute pain may be ineffective against chronic pain and drugs active, for example, against neuropathic pain may not be effective analgesics in other kinds of pain.

A variety of analgesic agents have been demonstrated as useful in the treatment of pain symptoms. Yet so far, the majority of available analgesics possess undesirable side effects.

Opioids are substances that act as agonists of opioid receptors in the CNS, and are considered as the most potent analgesic agents. Agents such as morphine and related opioid compounds, are often required for relief of severe pain. However, these narcotic drugs have the severe drawback of leading to dependence and addiction. In addition, patients treated with opioids tend to develop tolerance to the drug, which leads to increasing dosage of the drug needed for exerting the analgesic effect and to subsequent withdrawal symptoms. Further side effects associated with opioid drugs include nausea, sedation and respiratory depression.

Nonopioid analgesics, e.g. cyclooxygenase inhibitors such as acetaminophen (=paracetamol) and nonsteroidal anti-inflammatory drugs (NSAIDs) are often effective for treatment of mild to moderate pain. Anti-inflammatory agents of the NSAID class such as acetylsalicylic acid (aspirin), indomethacin, diclofenac and benzydamine have been used as analgesics in pain associated with trauma and inflammation. Nevertheless, clinical trials are still inconclusive. Common side effects of the NSAID class of drugs include: gastrointestinal irritation and ulceration, blockade of platelet aggregation, renal dysfunction and hepatic damage.

Another major class of analgesics is the local anaesthetics that block sodium channels. Compounds of this class, e.g. lidocaine, when topically applied to the spine, have been found effective for control of pain after surgery or trauma, but require expertise and infrastructure to administer and monitor properly. Systemic infusion of lidocaine can reduce acute pain, but requires continuous monitoring so that resuscitation from seizures or apnea can be performed immediately.

N-methyl-D-aspartate (NMDA) receptor antagonists are useful in treating neuropathic pain. It has been found that several sites on the NMDA receptor complex, activated by the excitatory amino acid glutamate, are analgesic targets. For example, Ketamine, which blocks the open calcium channel within this complex, has been suggested for use preoperatively or in neuropathic pain. Clinical studies confirm ketamine's merit as an analgesic or co-analgesic (e.g. with morphine). Nevertheless, psychotomimetic and other side effects such as salivation or cardiac stimulation restrict the applicability of standard doses of ketamine [Martindale: The Extra Pharmacopeia. 31$^{st}$ Edition. London: Pharmaceutical Press, (Editor Reynolds) 1996, pg. 1258–9].

Antidepressants, e.g. the tricyclic antidepressants amitriptyline and imipramine, and the serotonin re-uptake inhibitor paroxetine, have also been proven beneficial as analgesics. Tricyclic antidepressants can be helpful in several chronic pain states, especially in patients with head pain (including headache), central pain, and neuropathic pain. However, these drugs have the potential for adverse side effects, including anticholinergic effects and life-threatening cardiovascular effects.

Anticonvulsants have also been found to have useful analgesic effects. Gabapentin, has shown promise for the treatment of chronic pain [Rowbotham et al. (1998) JAMA 280: 1837–42] and carbamazepine and phenytoin, can be effective in the treatment of a range of neuropathic pain states. In particular, it has been found that trigeminal neuralgia responds well to carbamazepine [Green and Selman (1991) Headache 31: 588–592]. Sodium valproate has been reported as being effective in the prophylactic treatment of migraine [Hering & Kuritzky (1992) Cephalalgia 12: 81–84]. However, sodium valproate was found ineffective in the placebo controlled study in treating postoperative pain, which is an acute pain [Martin et al. (1988) *Ann FrAnesth Reanim* 7:387–92]. Some analogs of valproic acid that have been tested as potential anticonvulsant drugs were found sedative or had toxic effects [Keane et al. (1983) Neuropharmacology 22: 875–879].

Serious side effects that have been reported with anticonvulsant drugs, including deaths from hematological reactions, impaired mental and motor function, may limit clinical use, particularly in elderly people [Martindale: The Extra Pharmacopeia. 31$_{st}$ Edition. London: Pharmaceutical Press, (Editor Reynolds) 1996, pgs. 367–381]. Moreover, the results of several clinical trials with anticonvulsant drugs were disappointing and show conflicting results [McQuay et al. (1995) BMJ 311:1047–1052]. In particular, there is no evidence that anticonvulsants are effective for acute pain [Wiffen et al. (2000) The Cochrane Library, Issue 4, Oxford: Update Software].

Overall, it seems that the therapeutic effects of many of the existing analgesic agents are controversial and often inadequate. In addition, most of the currently available analgesic medicaments suffer from serious drawbacks which limit their use.

Clearly, there is an unmet clinical need for novel substances for effective treatment of various forms of pain, including acute and neuropathic pain.

SUMMARY OF THE INVENTION

The aim of the present invention is to provide methods for the treatment and/or prophylaxis of pain in mammals, in particular acute and neuropathic pain in humans.

Thus the present invention relates, in one aspect, to methods of treating or alleviating pain in mammals, comprising administering to a mammal suffering from pain, a pain-alleviating amount of a compound of the general formula (I) or (II) or pharmaceutically acceptable salts thereof.

The useful compounds according to the invention are of the general formula (I):

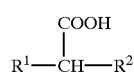
(I)

and pharmaceutically acceptable salts thereof, wherein:
$R^1$ is a saturated or unsaturated chain of 1–18 carbons in length; and
$R^2$ is a saturated or unsaturated chain of 1–18 carbons in length, with the proviso that $R^1$ and $R^2$ are not both propyl;
and compounds of the general formula (II):

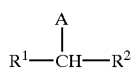
(II)

and pharmaceutically acceptable salts thereof, wherein:
$R^1$ is a saturated or unsaturated chain of 1–18 carbons in length; and
$R^2$ is a saturated or unsaturated chain of 1–18 carbons in length; and
A is selected from the group consisting of COOL and CONR'-R", wherein L is a lipid moiety selected from the group consisting of glycerol, $C_{3-20}$ fatty acid monoglycerides, $C_{3-20}$ fatty acid diglycerides, hydroxy-$C_{2-6}$-alkyl esters of $C_{3-20}$ fatty acids, hydroxy-$C_{2-6}$-alkyl esters of lysophosphatidic acids, lyso plasmalogens, lysophospholipids, lysophophatidic acid amides, glycerophosphoric acids, sphingolipids, lysophosphatidylethanolamine, and N-mono-($C_{1-4}$) alkyl and N,N-di-($C_{1-4}$)alkyl and quaternary derivatives of said lysophosphatidylethanolamine; and R' and R" are each independently selected from the group consisting of hydrogen and a lower alkyl group comprising 1–5 carbon atoms.

The methods encompassed by the invention, include methods for treatment and/or prophylaxis of pain in mammals, and in particular in humans. Said pain may be acute, chronic or neuropathic pain.

According to one preferred embodiment, the acute pain is selected from, but not limited to, post-operative pain, labor pain, toothache, pain induced by burns, muscle pain and pain accompanying myocardial infarction.

According to another preferred embodiment of the invention, the neuropathic pain is selected from, but not limited to, post-herpetic neuralgia, diabetic neuropathy, and trigeminal neuralgia.

According to yet another preferred embodiment, the treated pain is associated with a pathological condition or disease state which may be selected from, but not being limited to, the group consisting of stroke, spinal cord injury, inflammation condition, cancer, trigeminal neuralgia, arthritis, sickle cell disease, hemophilia, diabetes, herpes zoster and headache including cluster headache.

In currently preferred embodiments, the useful compounds are selected from the group consisting of:
2-Pentylheptanoic acid [M (5,5)],
2-Propyldodecanoic acid [M (3,10)],
2-Propylnonanoic acid [M (3,7)],
2-Heptylnonanoic acid [M (7,7)],
1-stearoyl-2-propylnonanoyl-sn-glycero-3-phosphocholine,
1-stearoyl-2-pentylheptanoyl-sn-glycero-3-phosphocholine,
1-stearoyl-2-heptylnonanoyl-sn-glycero-3-phosphocholine, and
1-stearoyl-2-propyldodecanoyl-sn-glycero-3-phosphocholine.

In another aspect, the present invention relates to compounds of the formula

wherein:
$R^1$ is a saturated or unsaturated chain of 6–18 carbons in length; and
$R^2$ is a saturated or unsaturated chain of 1–18 carbons in length; and
A is selected from the group consisting of COOL and CONR'-R", wherein L is a lipid moiety selected from the group consisting of glycerol, $C_{3-20}$ fatty acid monoglycerides, $C_{3-20}$ fatty acid diglycerides, hydroxy-$C_{2-6}$-alkyl esters of $C_{3-20}$ fatty acids, hydroxy-$C_{2-6}$-alkyl esters of lysophosphatidic acids, lyso plasmalogens, lysophospholipids, lysophophatidic acid amides, glycerophosphoric acids, sphingolipids, lysophosphatidylethanolamine, and N-mono-($C_{1-4}$) alkyl and N,N-di-($C_{1-4}$)alkyl and quaternary derivatives of said lysophosphatidylethanolamine; and R' and R" are each independently selected from the group consisting of hydrogen and a lower alkyl group comprising 1–5 carbon atoms; and pharmaceutically acceptable salts thereof.

In a preferred embodiment, the compounds of the invention are those including a lipid moiety at position A. More preferably the lipid moiety is a phospholipid. Currently most preferred compounds include a branched-chain derivative having a lyso-phosphatidylcholine moiety at position A.

In still another aspect, the present invention relates to pharmaceutical compositions for treating pain, comprising a pain-alleviating amount of a compound of the formula mentioned above and at least one pharmaceutically acceptable carrier.

Further objects of the present invention will become apparent to those skilled in the art upon further review of the following disclosure, including the detailed descriptions of specific embodiments of the invention.

DETAILED DESCRIPTION OF THE INVENTION

Figure 1:
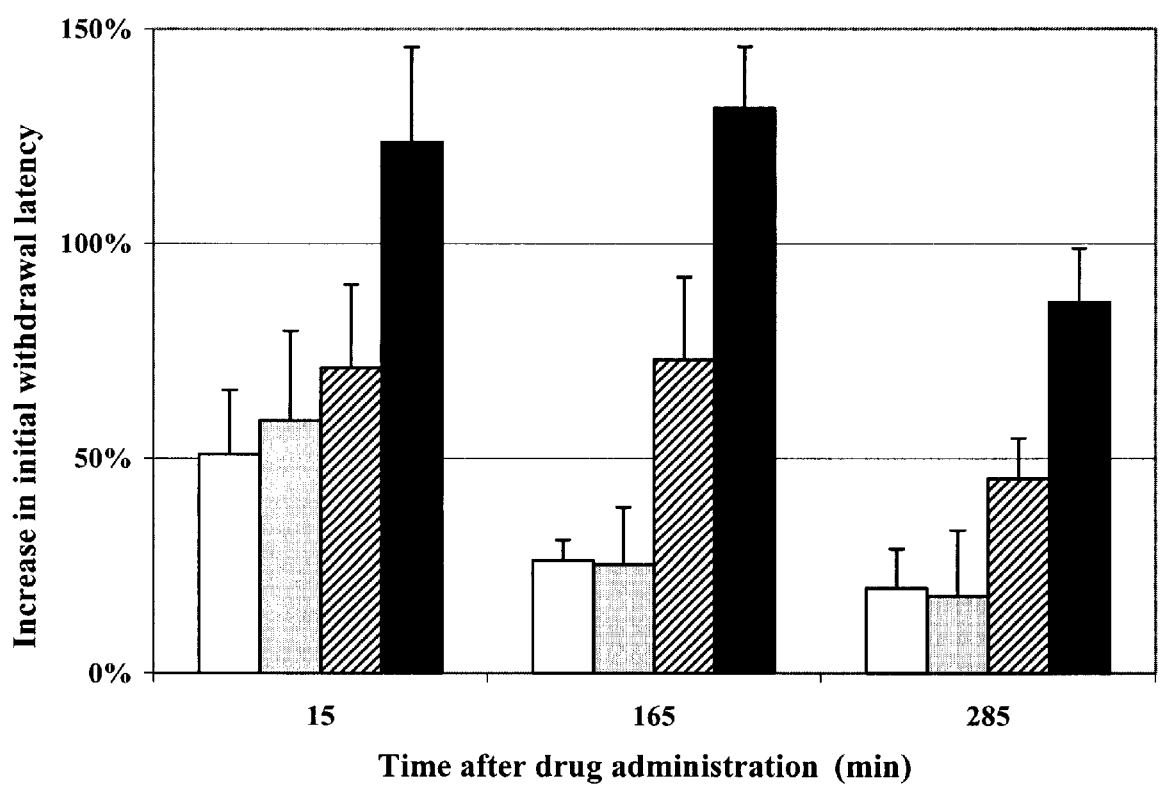
FIG. 1 depicts analgesic effects of 25 mg/kg (grey bars), 50 mg/kg (striped bars) and 100 mg/kg (dark bars) of DP-M(5,5) as tested in mice using the radiated heat 'tail flick' assay. The calculated percentage increase in the withdrawal latency in comparison to the initial withdrawal time (at t=0) is shown at different time points following i.p. administration of the drug. The white bars represent the control group of animals treated with vehicle only.

It is an object of the invention to provide new analgesic compositions suitable for the treatment of pain in mammals, and in particular for the treatment of acute and neuropathic pain in humans.

A desirable analgesic agent is a compound capable of exerting its favourable analgesic effect by effectively reducing or alleviating pain sensations, while having reduced or no side effects. In addition, a long-lasting analgesic effect of the drug may also be found beneficial in some cases of pain treatment.

According to the invention, compounds of the general formulas I and II and pharmaceutically acceptable salts thereof are useful for treatment of pain, that includes acute and chronic pain.

Unexpectedly, the inventors were now able to show that certain branched-chain fatty acids and derivatives thereof have marked effect against acute pain, as is demonstrated by studies using acceptable animal model systems.

Moreover, it has now been found that, surprisingly, some members of the family of compounds of the general formula I, which were not shown to be effective anticonvulsants in assays previously described in the parent application US 09/462,533 (International publication WO 99/02485), have significant analgesic activity.

In the specification, the branched-chain fatty acid compounds of the general formula I, or pharmaceutical acceptable salts thereof, will be collectively referred to as "BFAs". Specific BFAs will be referred to, hereinafter, according to the number of carbons in their particular $R^1$ and $R^2$ alkyl chains. For example, valproic acid which has propyl groups at both $R^1$ and $R^2$ positions, is defined as M(3,3). Similarly, 2-propylnonanoic acid is defined as M(3,7), 2-heptylnonanoic acid is defined as M(7,7) etc.

$R^1$ and $R^2$ alkyl chains of BFAs may be straight or branched chains, saturated or unsaturated chains having one or more double and/or triple bonds.

The salt forms of the branched fatty acids will be referred to by a suffix including the salt symbol. For example, the sodium salt form of 2-propylnonanoic acid is defined as M(3,7)-Na.

Suitable salts of the compounds of the general formula I include any pharmaceutically acceptable counter ion. In certain preferred embodiments the counter ion is selected from, but not limited to, $Na^+$, $Li^+$, $K^+$, $NH^{4+}$, $Ca^{++}$ and mixtures of these ions.

Derivatives of branched-chain fatty acids of the general formula II and pharmaceutically acceptable salts thereof are also useful analgesic compounds in accordance with the invention. These compounds in which the hydrogen atom of the carboxyl group of the branched fatty acid is replaced by a lipid moiety (ester derivatives of BFAs), or the hydroxyl group of the carboxyl group is replaced by an amine group (amide derivatives of BFAs), will hereinafter be collectively referred to as "DP-BFAs".

The BFAs and DP-BFAs compounds can be prepared essentially by the processes described in U.S. application Ser. No. 09/462,533, (the disclosure of which is herein incorporated in its entirety by reference), or by similar or alternative processes as they are known in the art.

As mentioned above, the branched-chain lipophilic molecules may be used as free acids, their physiologically acceptable salts or mixtures thereof, esters and amides.

Currently preferred useful compounds in accordance with the invention include the fatty acid residues 2-Pentylheptanoic acid [M(5,5)], 2-Propyldodecanoic acid [M(3,10)], 2-Propylnonanoic acid [M(3,7)] and 2-Heptylnonanoic acid [M(7,7)]. Both the free acid and salt forms of the compounds are useful analgesics in accordance with the invention.

Other preferred useful compounds are derivatives of BFAs (=DP-BFAs) wherein the hydrogen atom of the carboxyl group of the BFA is replaced by a lipid moiety, preferably a polar lipid and more preferably a phospholipid. Thus, the preferred embodiments of the invention encompass the use of the following DP-BFA compounds: 1-stearoyl-2-propylnonanoyl-sn-glycero-3-phosphocholine, 1-stearoyl-2-propyldodecanoyl-sn-glycero-3-phosphocholine, 1-stearoyl-2-pentylheptanoyl-sn-glycero-3-phosphocholine and 1-stearoyl-2-heptylnonanoyl-sn-glycero-3-phosphocholine.

Of the preferred members of both Formula I and formula II, the currently most preferred compounds are 2-Pentylheptanoic acid and 1-stearoyl-2-pentylheptanoyl-sn-glycero-3-phosphocholine.

It is important to note that when a DP-BFA molecule of the general formula II includes a glycerol based moiety at position A of the compound of the general formula II, the branched fatty moiety may be linked to the glycerol-based moiety at any one of positions sn-1, sn-2 or sn-3. Linkage at position sn-2 of a phospholipid, namely BFA linked to a lyso-phospholipid moiety, is preferred in accordance with the invention.

The DP-BFAs in accordance with the invention may be active per se or as prodrugs, which may be cleaved by an enzymatic or non-enzymatic reaction, preferably at the target site. For example, it has been reported that increase of phospholipase $A_2$ activity is associated with inflammation and neuropathic pain [Kawakami (1998) Clin Orthop. 351:241–51; Saal et al. (1990) Spine 15:674–8]. Hence, BFAs which are bound, for example, to a phospholipid at the sn-2 position, may be released by these enzymes whose activity is elevated at the site of pain.

The preferred type of lipid moiety selected for the generation of a DP-BFA compound, may depend on the specific disorder or pathology associated with the pain and its location. For example, sphingolipids which are found especially in nervous tissue and cell membranes may be preferred lipids in the case where the analgesic compound is to be targeted to the brain or other CNS tissues.

The DP-BFAs compounds, being amphiphilic in nature, may penetrate biological membranes and barriers, thus facilitating the transport of the drug into privileged tissues and organs. Moreover, the DP-BFA drugs, having the BFAs covalently linked to a lipophilic moiety, may exhibit favourable therapeutic activity e.g. improved pharmacokinetic properties and potency. Indeed, it was shown by the inventors of the present invention that the DP-BFA derivatives are more advantageous drugs in at least two aspects: (i) they are more potent as having increased analgesic effect on a molar basis in comparison to the corresponding branched-chain fatty acids, and (ii) their effect generally lasts for longer time, thus making them effective drugs for the treatment of chronic pain.

In addition at least some of the DP-BFAs were found to be much less sedating compared to their branched-chain fatty acids counterparts, therefore DP-BFAs are expected to exhibit reduced side effects and toxicity.

Any suitable route of administration is encompassed by the invention including, but not limited to, oral, intravenous, intramuscular, subcutaneous, inhalation, intranasal, topical, rectal, epidural, systemic transdermal application or other known routes.

In one preferred embodiment, the useful pharmaceutical compositions of the invention are administered orally or intravenously. In another preferred embodiment the route of administration is by topical application. Preferred embodiments of the topical application include nasal and ocular applications.

The pharmaceutical compositions may be in a liquid, aerosol or solid dosage form, and may be formulated into any suitable formulation including, but not limited to, solutions, suspensions, micelles, emulsions, microemulsions, ointments, gels, patches, suppositories, capsules, tablets, and the like, as will be required for the appropriate route of administration.

Compositions for oral administration may include, but are not limited to, powders or granules, suspensions or solutions in water or non-aqueous media, sachets, capsules or tablets. Thickeners, diluents, flavorings, dispersing aids, preservatives, emulsifiers or binders may be desirable.

Formulations for topical administration may include, but are not limited to, lotions, ointments, gels, creams, suppositories, drops, liquids, sprays and powders. Conventional pharmaceutical carriers, aqueous, powder or oily bases, thickeners and the like may be added. In the case of topical application, the composition including a pain-alleviating amount of a compound of the general formula I or II, is preferably applied on or in close proximity to the tissue associated with the pain.

Administration may follow the injury that induces the pain sensation, or alternatively may precede the insult or stimuli that are likely to provoke pain. On early administration, medicaments including the analgesic compounds of the general formula I or II, will be useful as prophylactic medicaments that may prevent, delay or alleviate the progression of pain symptoms. For example, the useful compounds, in accordance with the invention, may be administered to a patient before going through a surgical procedure, a painful dental treatment, entering the final stages of labor contractions etc., thus resulting in prevention, amelioration or reduction in the levels of post-operative or other pain.

The dose ranges for the administration of the compositions of the invention are those large enough to produce the desired analgesic effect.

For treating acute pain, the compounds of the general formula I or II may be employed at a daily dosage in the range of from about 0.01 gram to about 10 grams.

The dosing range of the medicament varies with the route of administration and the condition of the patient suffering from pain. The dosage administered will also be dependent upon the age, sex, health, weight of the recipient, concurrent treatment, if any, frequency of treatment, severity of the symptoms and the specific nature of the pain to be treated. In addition, dosage should be modified according to the patient response, as it is common in the practice that the tolerance thresholds of patients and their perception of painful sensation may be quite different. Dosage regimen and means of administration will be determined by the attending physician or other person skilled in the art.

The invention will now be illustrated by the following non-limiting examples.

EXAMPLES

The useful compounds in accordance with the invention, can be prepared by processes as described below in Examples 1 to 3, or by any alternative processes as they are known in the art.

It should be appreciated that while, for the sake of clarity, the following discussion and synthesis examples relate to straight-chain saturated members of the BFAs and DP-BFAs families, also branched and unsaturated BFAs and DP-BFAs, are included within the useful compounds in accordance with the disclosure of the present invention.

EXAMPLE 1

Synthesis of 2-Pentylheptanoic Acid [M(5,5)]

Anhydrous tetrahydrofuran (THF, 900 ml) and diisopropylamine (121.97 g, 1.208 mol) were added to a dry argon flushed flask under an atmosphere of argon. n-Butyllithium in hexane (740 ml of 1.6 M, 1.184 mol) was added to the magnetically stirred solution at such a rate as to maintain the temperature below 0 C. n-Heptanoic acid (80.81 g, 0.62 mol) was then added to the cold basic solution and again the temperature was kept below 0 C. After 15 min, HMPA (230 ml, 1.28 mol) was added to the milky white solution, which, after 5 min of stirring at 5 C, became transparent and light yellow. The solution was then stirred for an additional 15 min at 5 C, and n-Pentyl bromide (89.32 g, 0.592 mol) was added at once at 0 C. The reaction temperature immediately rose to 18–20 C. After 2 hours of additional stirring at room temperature, the reaction was processed in the following manner. Dilute hydrochloric acid (10%) was added at 0 C until the mixture became acidic. The aqueous layer was separated and extracted with petroleum ether (bp 30–60 C). The combined organic layers were washed with dilute hydrochloric acid and $H_2O$. The organic layer was then dried and the solvent was removed. The residue was distilled. Yield was 87 g (73%) of colorless oil, bp. 85–90 (1 mm Hg).

TLC analysis: Silica gel 60 F254 on aluminum sheet. Eluent is a mixture of pentane with ether (8:2 v/v).

2-Pentylheptanoic Acid [M(5,5)]

Colorless oil, Bp. 85–90 C (1 mm Hg). Yield =73%.

TLC analysis: One spot. $R_f$=0.42.

NMR (CDCl3),δ (ppm): 0.85–0.95 (m, 6H), 1.28–1.33 (broad s, 12H), 1.47–1.50 (m, 2H), 1.56 (m, 2H), 2.31 (m, 1H). MS (ES, negative. ions mode)=198.99 (M–H)[31]

The procedure for preparation of other BFAs is analogues to the synthesis of the 2-Pentylheptanoic acid mentioned above. The analysis was performed on TLC under the conditions as mentioned above.

2-Propyldodecanoic Acid [M(3, 10)]
Colorless oil, Bp. 128–138 C (1 mm Hg). Yield=77%.
TLC analysis: One spot. $R_f$=0.5.
NMR (CDCl$_3$),δ (ppm): 084(m, 6H), 1.2–1.33 (18H), 1.43 (m. 2H), 1.59 (m.2H), 2.35 (m.1H). MS (ES, negative. ions mode)=241.13. (M–H)[31]

2-Propylnonanoic Acid [M(3, 7)]
Colorless oil, Bp. 128–135 C (1 mm Hg). Yield=75%.
TLC analysis: One spot. $R_f$=0.46.
NMR (CDCl$_3$),δ (ppm): 084(m, 6H), 1.2–1.33 (10H), 1.43 (m. 2H), 1.59 (m.2H), 2.35 (m.1H). MS (ES, negative. ions mode)=199 (M–H)[31]

2-Heptylnonanoic Acid [M(7,7)]
Colorless oil, Bp. 128–135 C (1 mm Hg). Yield=75%.
TLC analysis: One spot. $R_f$=0.46.
NMR (CDCl$_3$),δ (ppm): 084 (m, 6H), 1.2–1.33 (10H), 1.43 (m. 2H), 1.59 (m.2H), 2.35 (m.1H). MS (ES, negative. ions mode)=254.4 (M–H)

2-Propyleicosanoic Acid [M(3, 18)]
Colorless oil, M.p. 55.6–57.4. Yield=75%.
TLC analysis: One spot. $R_f$=0.39.
NMR (CDCl$_3$),δ (ppm): 084 (m, 6H), 1.2–1.33 (34H), 1.43 (m. 2H), 1.59 (m.2H), 2.35 (m.1H). MS (ES, negative ion mode)=353.4 (M–H)[31].

The synthesis of the salt forms of branched-chain fatty acids is exemplified below by the synthesis procedure for 2-heptylnoanoic acid sodium salt.

Anhydrous ethanol (120 ml) and 2-heptylnonanoic acid (10 gr, 0.039 mol) were added to a dry argon flushed flask under an atmosphere of argon. Sodium ethylate (69.92 ml of 0.53 M, 0.037 mol) was added to the magnetically stirred solution at room temperature. After 5–6 hours the solvent was removed. The 2-heptylnonanoic acid sodium salt was re-crystallized from acetone.

Sodium titration is 100%. NMR analysis is the same as for the 2-heptylnonaoic acid.

EXAMPLE 2

Synthesis of 1-stearoyl-2-propylnonanoyl-sn-glycero-3-phosphocholine

The synthesis of 1-stearoyl-2-propylnonanoyl-sn-glycero-3-phosphocholine is a two-stage process. The first stage is the preparation of 2-propylnonanoic anhydride. The second stage includes binding of the BFA to the lipid moiety, in this case a lyso-lecithin, and isolation of the final product.

STAGE I. SYNTHESIS OF 2-PROPYLNONANOIC ANHYDRIDE.

In a round-bottom single-neck flask (250 ml), equipped with a reverse condenser (water cooling) and magnetic stirrer, 2-propylnonanoic acid (100 g, 0.5M), acetic anhydride (analytical, 400 ml, 1.06M) and pyridine (analytical, 44 ml, 0.5M) were introduced. This reaction mixture was stirred by magnetic stirrer for 4 hours at 70 C. After that acetic anhydride was evaporated at a pressure of 20 mm Hg. Residue was distilled at 1 mm Hg and fraction which is boiling at 150–152 C was collected. This is 2-propylnonanoic anhydride. Yield was 85% (81.1 g).

Analyses: TLC is performed on plates of Silica gel 60 F254 (Merck). Eluent is chloroform (analytical). One spot was visible in UV spectra. Rf=0.89.

Elemental analysis: $C_{24}H_{46}O_3$. Calculated: C 75.39%, H 12.04%. Found: C 75.25%, H 11.95%.

STAGE II. SYNTHESIS OF 1-STEAROYL-2-2-PROPYLNONAYL-sn-GLYCERO-3-PHOSPHOCHOLINE.

Lyso-lecithin (1-stearoyl-sn-glycero-phosphatidylcholine; 2 g, 3.82 mM), sodium salt of valproic acid (0.7 g, 4.2 mM) and 2-propyl-nonanoic anhydride (20 ml) were introduced under argon into a round-bottom single-neck flask (500 ml), equipped with a reverse condenser (water cooling) and magnetic stirrer. The reaction mixture was heated in oil bath (80–100 C) until disappearance of the lyso-lecithin (TLC monitoring) in the solution (about 3 hours of heating). The unreacted valproic anhydride was then distilled from the reaction flask by heating (110–120 C) under vacuum (about 0.1 mm Hg). The residue was dissolved in chloroform and the precipitate of sodium salt of valproic acid was separated from the solution by centrifugation. The obtained solution was concentrated by heating in an evaporator. After cooling, the chloroform solution of the reaction product was filtered on a chromatography column composed of Silica gel 60 (70–230 mesh). For purification of 1 gr. of raw reaction product 30 gr. of Silica gel are used. A mixture of chloroform, methanol and water (65:35:5 v/v) is used as an eluent. 2-propylheptyl acetic acid and its unreacted anhydride appear with the front of the eluent. The product is a white wax. After chromatography, purification of the product is performed by washing with n-pentane (three washes, each using a 20 ml portion). The obtained product was dried in vacuum at 40° C. Yield was 60% (1.5 g)

TLC analysis: Silica gel 60 F254 on aluminum sheet. Eluent is chloroform (stabilized by amylene). One spot was visible in UV spectra. Rf=0.3.

Elemental analysis: $C_{38}H_{76}O_8NP$. Calculated: C 64.62%, H 10.77%, N 2.00%, P 4.39%. Found: C:64.00%, H 10.9%, N 2.21%, P 4.4%. $^1$H NMR. (CDCl3), δ (ppm): 0.86–0.92 (m, 9H), 1.26 (broad s, 42H), 1.42–1.44 (m, 2H), 1.53–1.61 (m, 4H), 2.24–2.34 (m, 3H), 3.38 (s, 9H), 3.81–4.45 (broad m, 8H) and 5.20–5.28 (m,1H). $^{31}$p NMR (CDCl3), δ (ppm): -3.0 (respectively $H_3PO_4$ in $D_2O$) (s)

Analysis data for some specific DP-BFA molecules are listed below.

1-stearoyl-2-propylnonanoyl-sn-glycero-3-phosphocholine.
Elemental analysis: M 2H$_2$O (calculated/found %): C=61.54/62.18±0.51, H=10.79/10.40±0.15, N=1.89/1.71±0.05, P=4.18/4.04. MS (ES, positive ions mode)=706 (M+H)$^+$. TLC: Silica gel 60 F254 on aluminum sheet. Eluent is mixture of chloroform-methanol-water (64:25:4). One spot. $R_f$=0.68.
NMR (CDCl$_3$), δ (ppm): 084(m, 9H), 1.25–1.37 (40H), 1.41 (m. 2H). 1.49–1.59 (m.4H), 2.25–2.35(3H), 3.37 (9H), 3.38–4.48 (8H), 5.2 (m, H).

1-stearoyl-2-pentylheptonanoyl -sn-glycero-3-phosphocholine.
Elemental analysis: M 2H$_2$O (calculated/found %): C=61.54/61.36±0.05, H=10.79/9.91±0.34, N=1.81/1.75±00.4, P=4.18/3.65. MS (ES, positive ions mode)=706 (M+H)$^+$. TLC: Silica gel 60 F254 on aluminum sheet. Eluent is mixture of chloroform-methanol-water (64:25:4). One spot. $R_f$=0.67.
NMR (CDCl$_3$), δ (ppm): 084(m, 9H), 1.25–1.37 (48H), 1.41 (m. 2H), 1.49–1.59 (m.4H), 2.25–2.35(3H), 3.37 (9H), 3.38–4.48 (8H), 5.2 (m, H).

1-stearoyl-2-heptylnonanoyl -sn-glycero-3-phosphocholine.
Elemental analysis: M 1H$_2$O (calculated/found %): C=64, 70/64,05±0.08, H=11,04/11,21±0.13, N=1.80/1.81±00.3, P=4.0/3.02. MS (ES, positive ions mode)=762 (M+H)$^+$.
TLC: Silica gel 60 F254 on aluminum sheet. Eluent is mixture of chloroform-methanol-water (64:25:4). One spot.

$R_f=0.73$. NMR (CDCl$_3$), δ (ppm): 084(m, 9H), 1.25–1.37 (48H), 1.41 (m. 2H), 1.49–1.59 (m.4H), 2.27–2.35(3H), 3.22 (9H), 3.38–4.48 (8H), 5.2 (m, H).

1-O-stearoyl-2-propyldodecanoyl -sn-lycero-3-phosphatidylcholine [DP-M (3,10)]

Elemental analysis: M 2H2O (calculated/found %): C=63.56/63.52±0.12, H=11.24/10.33±0.03, N=1.80/1.65±00.4, P=4.00/4.28. MS (ES, positive ions mode)=749 (M+H)$^+$.

TLC: Silica gel 60 F254 on aluminum sheet. Eluent is mixture of chloroform-methanol-water (64:25:4). One spot. $R_f=0.71$.

NMR (CDCl$_3$), δ (ppm): 084(m, 9H), 1.28–1.35 (46H), 1.41 (m. 2H), 1.59 (m.4H), 2.27–2.33(3H), 3.22 (9H), 3.38–4.48 (8H), 5.2 (m, H).

EXAMPLE 3

Synthesis of 2-Propyloctadecanamide [DP-M(3,16)-amide]

The synthesis of the amide analogs of the branched chain fatty acid is exemplified below by the synthesis procedure for 2-propyloctadecanamide [DP-M(3,16)-amide].

The synthesis of the amide derivatives of BFAs compounds is a two-step procedure. The chloride derivative of the branched chain fatty acid is prepared at the first stage, followed by the addition of the amide itself at the second stage. The other DP-amnides are prepared according to an analogous procedure to the synthesis of 2-propyloctadecanamide described below.

Overall, the synthesis can be described according to the following synthetic pathway:

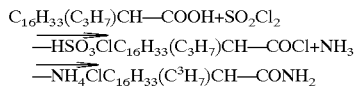

2-Propyloctadecanoic acid (200 mg, 0.61 mmol) was introduced into a single neck round-bottom flask, equipped with a magnetic stirrer and a reverse condenser. Three milliliters of SO$_2$Cl$_2$ were also placed in the flask. The reaction mixture was brought to reflux and left for one hour. The reaction mixture was then evaporated. Dry benzene (5 ml) was added to the residue and then evaporated. This procedure was repeated twice. The resultant residue was dissolved in 5 ml of dry tetrahydrofuran and then 0.2 ml of 0.5 M ammonia in dioxane was added to this solution. The suspension thus obtained was stirred with a magnetic stirrer for one hour and then evaporated. Petroleum ether was added to the residue and the mixture was stirred. The obtained solid was filtered, and then washed twice with water and petroleum ether. The precipitate was dried under vacuum (10 mm Hg) for three hours at room temperature. The product was a white powder. The yield was 80%.

2-Propvyloctadecanamide [DP-M(3.16)-amide]

The product was a white powder with a yield of 80%.

TLC analyses: Silica gel 60 on aluminum sheet. Eluent was a mixture of petroleum ether with diethyl ether (3:7, v/v). Indicator was a spray of 4-methoxybenzaldehyde (10 ml), abs. ethanol (200 ml), 98% sulfuric acid (10 ml), glacial acetic acid (2 ml). The chromatogram was sprayed with this indicator, dried and then charred at 100–150° C. One spot was observed. $R_f=0.2$.

Elemental analysis: C$_{23}$H$_{47}$NO. Calculated: C 78.19%, H 13.31%, N 3.97%. Found: C 78.09%, H 13.11%, N 3.77%. $^1$H NMR. (CDCL$_3$), δ (ppm): 0.84–0.93 (m, 6H), 1.24–1.41 (m, 34H), 1.52–1.60 (broad s, 4H), 2.06–2.15 (m,1H) and 5.30–5.36 (d, 2H).

Analysis data for additional DP-BFA-amide molecules are listed below.

2-Propyl-nonamide [DP-M(3, 7)-amidel]

The product was a white powder with a yield of 75%.

TLC analyses: Silica gel 60 on aluminum sheet. Eluent was a mixture of petroleum ether with diethyl ether (3:7, v/v). Indicator was a spray of 4-methoxybenzaldehyde (10 ml), abs. ethanol (200 ml), 98% sulfuric acid (10 Ml), glacial acetic acid (2 ml). The chromatogram was sprayed with this indicator, dried and then charred at 100–150° C. One spot was observed. $R_f=0.2$.

Elemental analysis: C$_{12}$H$_{25}$NO. Calculated: C 72.36%, H 12.56%, N 7.04%. Found: C:72.50%, H 12.81%, N 7.22%. $^1$H NMR. (CDCL$_3$), δ (ppm): 0.85–0.94 (m, 6H), 1.22–1.42 (m, 14H), 1.51–1.60 (m, 2H), 2.06–2.18 (m,1H) and 5.32–5.44 (d, 2H).

2-Propylhexadecanamide [DP-M(3,14)-amide]

The product was a white powder with a yield of 80%.

TLC analyses: Silica gel 60 on aluminum sheet. Eluent was a mixture of petroleum ether with diethyl ether (3:7, v/v). Indicator was a spray of 4-methoxybenzaldehyde (10 ml), abs. ethanol (200 ml), 98% sulfuric acid (10 ml), glacial acetic acid (2 ml). The chromatogram was sprayed with this indicator, dried and then charred at 100–150° C. One spot was observed. $R_f=0.2$.

Elemental analysis: C21H$_{43}$NO. Calculated: C 77.53%, H 13.23%, N 4.30%. Found: C 77.56%, H 13.39%, N 4.39%. $^1$H NMR. (CDCL$_3$), δ (ppm): 0.86–0.92 (m, 6H), 1.24–1.43 (m, 30H), 1.52–1.60 (m, 4H), 2.08–2.12 (m,1H) and 5.28–5.36 (d, 2H).

EXAMPLE 4

Effects of BFAs and their Derivatives Tested in Tail-flick Assay (A model System for Acute Pain)

The analgesic effect of branched-chain fatty acids (BFAs) and their DP-BFAs derivatives was tested by using the tail flick assay in mice.

The tail-flick test is a heat nociception test initially employed by D'Amour and Smith [D'Amour and Smith (1941) J. Pharmacol. Exp Ther. 72:74–79] and is a widely used animal model system for quantitative measurements of acute pain threshold. This model uses radiated infrared (IR) heat source that is directed to the tail of a restrained mouse. The threshold of tolerance for heat is indicated by a timemeter, which is stopped instantaneously when the tail flicks. This time is defined as 'withdrawal latency'.

Male CD-1 mice weighing around 25–30 grams (4–8 animals per each dose of the tested compound) were used. The animals were put in clear plastic cages above an IR source (7371-Plantar™ Analgesia Instrument, UGO Basile), where the IR generator is placed directly underneath the tail of the mouse and the light beam is focused on the proximal third of the tail.

The withdrawal latency, namely the time interval from the starting of the infrared radiation until the animal feels pain and flicks its tail is determined.

The initial withdrawal latency for each animal was measured at t=0 and was determined as its baseline threshold.

In order to determine the analgesic effect of a tested drug, the drug (10 to 200 mg/kg body weight) was intraperitoneally (i.p.) injected to the mice. Withdrawal latency was determined at different time points post-injection as indicated. Each reading was performed 2–3 times and the mean value was calculated. Withdrawal latencies of the treated animals, expressed as percentage of the withdrawal latency of the control group of animals treated with vehicle alone, are shown Table 1. The withdrawal latency at each time point post injection is the average of 4–8 animals per group. Withdrawal latency at t=0 for all tested animal was around 9 to 12 seconds. Paired T-test was used to assess significance in comparison to the baseline value (t=0). Morphine was used as a positive control(2 animals per dose).

TABLE 1

Analgesic effects of BFAs and DP-BFAs measured in tail flick assay

| Compound | Dose (mg/kg) | Withdrawal latency (% of vehicle) Time post-injection (min) | | | | | | |
|---|---|---|---|---|---|---|---|---|
| | | 15 min | 45 min | 75 min | 105 min | 135 min | 285 min | 345 min |
| Morphine | 1 | 107% | 89% | 120% | 82% | | | |
| | 2 | 181% | 136% | 108% | 125% | | | |
| M(3,7) | 150 | 157% | 137% | 106% | 131% | | | |
| M(3,10) | 100 | 142% | 155% | 131% | 156% | 123% | | |
| | 200 | 186% | 210% | | 183% | | | |
| M(3,10)-Na | 50 | 151% | 138% | 128% | 123% | 102% | | |
| | 100 | 181% | 153% | 121% | 143% | 148% | | |
| | 200 | 158% | 220% | 216% | 141% | 175% | | |
| M(5,5) | 200 | 161% | 135% | 145% | 158% | | | |
| M(5,5)-Na | 50 | 115% | 124% | 117% | 134% | | | |
| | 100 | 137% | 164% | 164% | 193% | | | |
| M(7,7) | 200 | 93% | 124% | 117% | 149% | 124% | | |
| DP-M(3,7) | 50 | 132% | 123% | 119% | 102% | 112% | 119% | 114% |
| | 100 | 127% | 156% | 124% | 114% | 126% | 127% | 125% |
| DP-M(3,10) | 50 | 123% | 119% | 113% | 123% | 123% | 129% | 107% |
| DP-M(5,5) | 50 | 113% | 107% | 118% | 142% | 152% | 121% | 124% |
| | 100 | 148% | 143% | 148% | 162% | 171% | 155% | 124% |

As shown in Table 1, a statistically significant increase in withdrawal latency, indicating an increase in the animal pain threshold, can be seen with the different amounts of the BFAs and DP-BFAs molecules. The largest analgesic effects in this experiment were demonstrated with 1-stearoyl-2-pentylheptonanoyl-sn-glycero-3-phosphocholine, 2-Pentylheptanoic acid and 2-Propyldodecanoic acid.

The most potent drug in this assay was DP-M(5,5), which was, on a molar basis, about 3-4 times more potent than M(5,5).

It is important to note that the tested compounds exerted their analgesic effect in a dose dependent fashion (results for DP-M(5,5) are shown in FIG. 1).

It should also be pointed out that duration of the analgesia effect with most tested BFA compounds in this model system was for about 1.5–2 hours following dosing. With the lipid derivatives, DP-BFAs, a significant effect was demonstrated for up to 5–6 hours post injection. Prolonged effect of the drugs was also demonstrated with subcutaneously (s.c.) injected DP-M(5,5), where 40–60% increase in withdrawal latency of animals treated with 50 and 100 mg/kg DP-M(5, 5), in comparison to the vehicle-treated animals, was shown at 5–6 hours post injection.

Generally, the animals treated with the DP-BFA derivatives were less sedative in comparison to the animals treated with the corresponding BFAs compounds.

Conclusions: The results of the "tail-flick" study demonstrate that BFAs and DP-BFAs compounds are effective in reducing acute pain sensation.

EXAMPLE 5

Effects of BFAs Tested in Writhing Assay (a Model for Peripheral Acute Pain)

The analgesic effects of BFAs were evaluated in an animal model system for peripheral acute pain, the writhing model system.

The writhing model represents a chemical nociception test, based on the induction of a peritonitis-like condition in the animals by injecting irritant substances intraperitoneally (i.p.). The writhing test is a simple and reproducible assay, which is characterized by repeated contractions of the abdominal muscles accompanied by extension of the hindlimbs of the animal (Jaques, Arzneimittelforschung, 27, 1698–70, 1977: Siegmund et al, Proc. Soc. Exp. Biol. 95:729:731, 1957).

Pain is induced in CD-1 mice by i.p. injection of acetic acid (0.6%, 10ml/kg in $ddH_2O$). The number of writhes (abdominal constriction followed by dorsiflexion and extension) occurring during a 15 min. time period is recorded, starting 5 minutes after acetic acid administration.

Average of around 20 to 30 writhes were recorded during this period of time in animals injected with the acetic acid only or animals treated with vehicle.

The treated animals are subcutaneously (s.c.) injected, 30 minutes prior to the injection of the acetic acid, with different doses of the tested compounds in amounts ranging from 10 to 200 mg/kg body weight. Animals treated with vehicle only, serve as control.

Reduction in the number of writhes in response to acid that is injected following administration of the BFAs or DP-BFAs, demonstrates that these compounds may serve as effective analgesics useful for treatment of acute pain.

EXAMPLE 6

Effects of BFAs Measured in the Chronic Constriction Injury (CCI) Model System (Neuropathic Pain )

The chronic constriction injury (CCI) is an animal model system developed by Bennet and Xie [(1988) Pain 33: 87–107] for producing a chronic peripheral mononeuropathy in rodents.

Neuropathic pain is induced by loose ligation of the sciatic nerve and is characterized by hyperalgesia (increased sensitivity to painful stimuli) and allodynia (the sensitivity in response to normally innocuous stimuli).

Male, Sprague-Dawley (SD) rats, weighing around 200–250 grams, are anesthetized by i.p. injection of ketamine (50 mg/kg) and xylazine (10 mg/kg). The common sciatic nerve is exposed at the middle of the thigh of the hind left foot. Four ligatures are tied loosely around the nerve with a spacing of about 1mm between them. Then the incision is closed. Five to seven days later the nociception threshold is evaluated by quantifying sensitivity of the foot to mechanical stimuli or cold temperatures to assess allodynia. The mechanical sensitivity of the animal foot is measured using the von Frey test. A von Frey filament is applied to the plantar surface of the foot and the frequency of foot withdrawals is measured [Kim and Chung (1992) Pain 50: 355–63].

Cold sensitivity is quantified by monitoring brisk foot withdrawal in response to acetone. Acetone is applied to the plantar surface of the animal foot and the frequency of foot withdrawal is measured as described by Choi et al. [(1994) Pain 59:369–376].

In another set of experiments, hyperalgesia to noxious pain is quantified by using radiated infrared (IR) heat as the pain stimulus similarly to the procedure described above in Example 4 for the tail flick assay, except that in this case the IR is focused on the plantar hind paw of a rat. The withdrawal latency of the hind paw is recorded in animals pre-treated with various dosages of BFAs / DP-BFAs (10–200 mg/kg body weight) or vehicle only (control). The withdrawal latency is recorded at 15, 45, 75, 105 and 145 minutes following s.c. injection of the tested drug or vehicle solution. The determined withdrawal latency is compared to the initial withdrawal latency for each animal as measured at t=0 (baseline threshold), and to the withdrawal latency measured for the uninjured right hind foot.

Same behavioral tests aimed to establish nociceptive threshold values for naive uninjured rats, are conducted on all animals one day prior to surgery.

The analgesic effect of BFAs and DP-BFAs is tested by recording increase in the withdrawal latency measured for the injured left foot in the animals treated with these drugs. The analgesic effect is also assessed by the von Frey and cold sensitivity tests.

EXAMPLE 7

Hemisection Injury of Spinal Chord (Central Neuropathic Pain)

Spinal cord hemisection is an acceptable model system for inducing central chronic neuropathic pain.

Male Sprague-Dawley (SD) rats weighing around 200–250 grams are deeply anesthetized with ketamine (50 mg/kg) and xylazine (10 mg/kg). The spinal cord is hemisectioned at the level of T9 to T12 with a scalpel blade without damage to the surrounding vasculature. Then the incision is closed. Sham operated animals serve as a control group.

Behavioral tests representing mechanical and thermal allodynia as described above in Example 6 are performed pre-operatively and post-operatively for both hind limbs. The preoperative testing is performed one day prior to surgery and serves to establish both individual and group baseline behaviors. The tests are performed on alternate days, starting on the fifth to seventh day following surgery, and are carried on for up to 30 days. Mechanical allodynia of the paw is quantified by measuring the number of brisk paw withdrawals in response to normally innocuous mechanical stimuli applied by von Frey filaments [Christensen et al. (1996) Pain 68: 97–107].

The analgesic effect of the BFAs and DP-BFAs compounds is tested. A decrease in the number of paw withdrawals in response to stimuli by von Frey filaments is an indication for analgesia. The beneficial effects are also assessed in the thermal tests where increase in the withdrawal latency for the ipsilateral foot of the injured animals treated with the drugs is an indication for analgesic activity.

Conclusions: The tested branched-chain fatty acids and their DP-derivatives are potential analgesics that may serve for treating pain, including neuropathic pain.

The foregoing disclosure has been set forth merely to illustrate the invention and is not intended to be limiting. Persons skilled in the art will appreciate that many variations and modifications can be made which do not depart from the teaching of the present invention. Therefore, the invention is not to be construed as restricted to the particularly described embodiments, rather the scope, spirit and concept of the invention will be more readily understood by reference to the claims which follow.

We claim:

1. A method of treating or alleviating pain in mammals, comprising administering to a mammal suffering from pain, a pain-alleviating amount of a compound of the general formula I:

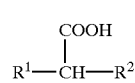

and pharmaceutically acceptable salts thereof, wherein:
$R^1$ is a saturated or unsaturated chain of 1–18 carbons in length; and
$R^2$ is a saturated or unsaturated chain of 1–18 carbons in length, with the proviso that $R^1$ and $R^2$ are not both propyl.

2. A method according to claim 1, wherein the mammal suffering from pain is a human.

3. The method according to claim 1, wherein the pain is other than chronic pain.

4. The method according to claim 1, wherein the pain is acute pain.

5. The method according to claim 4, wherein the acute pain is selected from the group consisting of post-operative pain, labor pain, toothache, pain induced by burns, muscle pain and pain accompanying myocardial infarction.

6. The method according to claim 1, wherein the pain is neuropathic pain.

7. The method according to claim 6, wherein the neuropathic pain is selected from the group consisting of post-herpetic neuralgia, diabetic neuropathy, and trigeminal neuralgia.

8. The method according to claim 1, wherein the pain is associated with a pathological condition or disease state.

9. The method according to claim 8, wherein said pathological condition or disease state is selected from the group consisting of stroke, spinal cord injury, inflammation condition, cancer, trigeminal neuralgia, arthritis, sickle cell disease, hemophilia, diabetes, herpes zoster and headache.

10. The method according to claim 1, wherein said compound of the general formula I is selected from the group consisting of:
2-Pentylheptanoic acid;
2-Propyldodecanoic acid,
2-Propylnonanoic acid, and
2-Heptylnonanoic acid.

11. The method according to claim 1, wherein the pain-alleviating amount of a compound of the general formula I is administered before onset of pain.

12. The method according to claim 1, wherein the compound of the general formula I is orally, intravenously or topically administered.

13. A method of treating or alleviating pain in mammals, comprising administering to a mammal suffering from pain, a pain-alleviating amount of a compound of the general formula II:

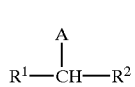

and pharmaceutically acceptable salts thereof, wherein:
$R^1$ is a saturated or unsaturated chain of 1–18 carbons in length; and
$R^2$ is a saturated or unsaturated chain of 1–18 carbons in length; and
A is selected from the group consisting of COOL and CONR'-R", wherein L is a lipid moiety selected from the group consisting of glycerol, $C_{3-20}$ fatty acid monoglycerides, $C_{3-20}$ fatty acid diglycerides, hydroxy-$C_{2-6}$-alkyl esters of $C_{3-20}$ fatty acids, hydroxy-$C_{2-6}$-alkyl esters of lysophosphatidic acids, lyso plasmalogens, lysophospholipids, lysophophatidic acid amides, glycerophosphoric acids, sphingolipids, lysophosphatidylethanolamine, and N-mono-$(C_{1-4})$ alkyl and N,N-di-$(C_{1-4})$alkyl and quaternary derivatives of said lysophosphatidylethanolamine; and R' and R" are each independently selected from the group consisting of hydrogen and a lower alkyl group comprising 1–5 carbon atoms.

14. A method according to claim 13, wherein the mammal suffering from pain is a human.

15. The method according to claim 13, wherein the pain is other than chronic pain.

16. The method according to claim 13, wherein the pain is acute pain.

17. The method according to claim 16, wherein the acute pain is selected from the group consisting of post-operative pain, labor pain, toothache, pain induced by bums, muscle pain and pain accompanying myocardial infarction.

18. The method according to claim 13, wherein the pain is neuropathic pain.

19. The method according to claim 18, wherein the neuropathic pain is selected from the group consisting of post-herpetic neuralgia, diabetic neuropathy, and trigeminal neuralgia.

20. The method according to claim 13, wherein the pain is associated with a pathological condition or disease state.

21. The method according to claim 20, wherein said pathological condition or disease state is selected from the group consisting of stroke, spinal cord injury, inflammation condition, cancer, trigeminal neuralgia, arthritis, sickle cell disease, hemophilia, diabetes, herpes zoster and headache.

22. The method according to claim 13, wherein said compound of the general formula II is selected from the group consisting of:
1-stearoyl-2-propylnonanoyl-sn-glycero-3-phosphocholine,
1-stearoyl-2-pentylheptonanoyl-sn-glycero-3-phosphocholine,
1-stearoyl-2-heptylnonanoyl-sn-glycero-3-phosphocholine, and
1-stearoyl-2-propyldodecanoyl-sn-glycero-3-phosphocholine.

23. The method according to claim 13, wherein the pain-alleviating amount of a compound of the general formula II is administered before onset of pain.

24. The method according to claim 13, wherein the compound of the general formula II is orally, intravenously or topically administered.

25. A compound of the formula

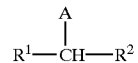

wherein:
$R^1$ is a saturated or unsaturated chain of 6–18 carbons in length; and $R^2$ is a saturated or unsaturated chain of 1–18 carbons in length; and A is selected from the group consisting of COOL and CONR'-R", wherein L is a lipid moiety selected from the group consisting of glycerol, $C_{3-20}$ fatty acid monoglycerides, $C_{3-20}$ fatty acid diglycerides, hydroxy-$C_{2-6}$-alkyl esters of $C_{3-20}$ fatty acids, hydroxy-$C_{2-6}$-alkyl esters of lysophosphatidic acids, lyso plasmalogens, lysophospholipids, lysophophatidic acid amides, glycerophosphoric acids, sphingolipids, lysophosphatidylethanolamine, and N-mono-$(C_{1-4})$ alkyl and N,N-di-$(CI_{1-4})$alkyl and quaternary derivatives of said lysophosphatidylethanolamine; and R' and R" are each independently selected from the group consisting of hydrogen and a lower alkyl group comprising 1–5 carbon atoms; and pharmaceutically acceptable salts thereof.

26. The compound of claim 25, wherein L is a phospholipid.

27. The compound of claim 25, wherein L is lysophosphatidylcholine.

28. The compound of claim 25, wherein L is lysophosphatidylcholine and $R^1$ and $R^2$ are each heptyl.

29. A composition for treating pain, comprising a pain-alleviating amount of a compound of the formula

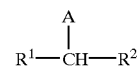

and pharmaceutically acceptable salts thereof, wherein:

$R^1$ is a saturated or unsaturated chain of 6–18 carbons in length; and $R^2$ is a saturated or unsaturated chain of 1–18 carbons in length; and A is selected from the group consisting of COOL and CONR'-R", wherein L is a lipid moiety selected from the group consisting of glycerol, $C_{3-20}$ fatty acid monoglycerides, $C_{3-20}$ fatty acid diglycerides, hydroxy-$C_{2-6}$-alkyl esters of $C_{3-20}$ fatty acids, hydroxy-$C_{2-6}$-alkyl esters of lysophosphatidic acids, lyso plasmalogens, lysophospholipids, lysophophatidic acid amides, glycerophosphoric acids, sphingolipids, lysophosphatidylethanolamine, and N-mono-$(C_{1-4})$ alkyl and N,N-di-$(C_{1-4})$alkyl and quaternary derivatives of said lysophosphatidylethanolamine; and R' and R" are each independently selected from the group consisting of hydrogen and a lower alkyl group comprising 1–5 carbon atoms; and at least one pharmaceutically acceptable carrier.

30. The composition according to claim 29, wherein L is phospholipid.

31. The composition according to claim 29, wherein said compound is 1-stearoyl-2-heptylnonanoyl-sn-glycero-3-phosphocholine.

* * * * *